(12) United States Patent
Goldstein et al.

(10) Patent No.: US 6,242,461 B1
(45) Date of Patent: Jun. 5, 2001

(54) USE OF ARYL SUBSTITUTED AZABENZIMIDAZOLES IN THE TREATMENT OF HIV AND AIDS RELATED DISEASES

(75) Inventors: Steven W. Goldstein, Noank; William G. Stirtan, East Lyme, both of CT (US); Brian A. Sherer, Clifton Park, NY (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/578,655

(22) Filed: May 25, 2000

Related U.S. Application Data

(60) Provisional application No. 60/177,920, filed on Jan. 25, 2000.

(51) Int. Cl.⁷ .................................................. A61K 31/435
(52) U.S. Cl. ............................................. 514/303; 546/118
(58) Field of Search .............................. 546/118; 514/303

(56) References Cited

FOREIGN PATENT DOCUMENTS

WO 91/17162 * 11/1991 (WO).

* cited by examiner

*Primary Examiner*—Bernard Dentz
(74) *Attorney, Agent, or Firm*—Peter C. Richardson; Paul H. Ginsburg; Jolene W. Appleman

(57) ABSTRACT

This invention relates to novel aryl substituted azabenzimidazoles of Formula (I) and pharmaceutically acceptable salts thereof.

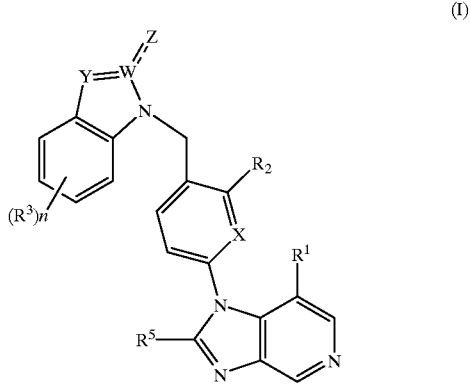

or a pharmaceutically acceptable salt thereof wherein
n is an integer from 1 to 4
X is CH or N;
$R^1$ is H, $(C_1-C_6)$alkyl or $(C_1-C_6)$ alkoxy;
$R^2$ is H, $(C_1-C_6)$alkyl or $(C_1-C_6)$ alkoxy;
each $R^3$ is independently selected from H, $(C_1-C_6)$alkyl $(C_1-C_6)$ alkyloxy, $(C_1-C_6)$ alkylthio, halo, nitro, cyano, ethynyl, hydroxy and trifluoromethyl;
$R^4$ is H, $(C_1-C_6)$alkyl or $(C_1-C_6)$ alkoxy;
$R^5$ is H, $(C_1-C_6)$alkyl or $(C_1-C_6)$ alkyloxy, trifluoromethyl; and
W is N or C;
Y is N $(R^4)$, N, S or O
Z is $R^4$, $NR^4H$, O, or OH;

Provided that when Y=NR⁴, W=C, Z=O, there is a single bond between YW and a double bond between WZ; and
when Y=O or S, W=C, Z=O, there is a single bond between YW and a double bond between WZ; and
when Y=N, W=N, there is a double bond between YW and Z does not exist.
when Y=N, W=C, Z=R⁴ or NHR⁴, there is a double bond between YW and a single bond between WZ; The methods of preparing these compounds and their use in the treatment of HIV, AIDS, and AIDS related diseases and in slowing the progression of HIV infection into AIDS is also disclosed.

9 Claims, No Drawings

USE OF ARYL SUBSTITUTED AZABENZIMIDAZOLES IN THE TREATMENT OF HIV AND AIDS RELATED DISEASES

This application claims priority from Provisional Application Ser. No. 60/177,920 filed Jan. 25, 2000.

BACKGROUND OF THE INVENTION

The invention relates to novel aryl substituted azabenzimidazoles and the pharmaceutically acceptable salts thereof, methods of preparing these compounds and the use of these compounds in the treatment of HIV, AIDS and AIDS related diseases and in slowing the progression of HIV infection into AIDS.

The human disease, Acquired Immune Deficiency Syndrome (AIDS), is caused by the Human Immunodeficiency Virus (HIV), particularly the strain known as HIV-1.

Like other viruses, HIV cannot replicate without commandeering the biosynthetic apparatus of the host cell it infects. HIV causes this biosynthetic apparatus to produce the structural proteins which make up the viral progeny. These proteins are coded for by the genetic material contained within the infecting virus particle, or virion. Being a retrovirus, however, the genetic material of HIV is RNA, not DNA as in the host cell's genome. Accordingly, the viral RNA must first be converted into DNA, and then integrated into the host cell's genome, in order for the host cell to produce the required viral proteins. The conversion of the RNA to DNA is accomplished through the use of enzyme reverse transcriptase (RT), which is included within the infecting virion along with the RNA. Reverse transcriptase has three enzymatic functions; it acts as an RNA-dependent DNA polymerase; as a ribonuclease; and as a DNA-dependent DNA polymerase. Acting first as an RNA-dependent DNA polymerase, RT makes a single-stranded DNA copy of the viral RNA. Next, acting as a ribonuclease, RT frees the DNA just produced from the original viral RNA and then destroys the original RNA. Finally, acting as a DNA-dependent DNA polymerase, RT makes a second, complementary DNA strand, using the first DNA strand as a template. The two strands form double stranded DNA, which is integrated into the host cell's genome by another enzyme called an integrase.

Compounds which inhibit the enzymatic functions of HIV reverse transcriptase will inhibit replication of HIV in infected cells. There is a high medical need for better tolerated, conveniently administered agents to treat AIDS which is increasingly viewed as a chronic disease. These agents should ideally reverse the development and progression of AIDS, in HIV infected individuals, reduce susceptibility to secondary infections, and return the patient to as near a normal lifestyle as possible.

SUMMARY OF THE INVENTION

The present invention comprises compounds of the formula

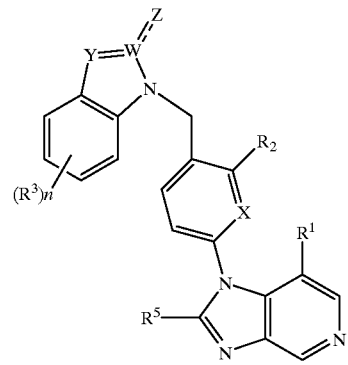

or a pharmaceutically acceptable salt thereof wherein n is an integer from 1 to 4;

X is CH or N;

$R^1$ is H, $(C_1-C_6)$alkyl or $(C_1-C_6)$ alkyloxy;

$R^2$ is H, $(C_1-C_6)$alkyl or $(C_1-C_6)$ alkyloxy;

each $R^3$ is independently selected from H, $(C_1-C_6)$alkyl, $(C_1-C_6)$ alkyloxy, $(C_1-C_6)$ alkylthio, halo, nitro, cyano, ethynyl, hydroxy and trifluoromethyl;

$R^4$ is H, $(C_1-C_6)$alkyl or $(C_1-C_6)$ alkoxy;

$R^5$ is H, $(C_1-C_6)$alkyl or $(C_1-C_6)$ alkoxy, trifluoromethyl; and

W is N or C;

Y is $N(R^4)$, N, S or O;

Z is $R^4$, $NR^4H$, O, or OH;

provided that when Y=$NR^4$, W=C, and Z=O, there is a single bond between YW and a double bond between WZ; and when Y=O or S, W=C, and Z=O, there is a single bond between YW and a double bond between WZ; and when Y=N, W=C, Z=$R^4$ or $NHR^4$, there is a double bond between YW and a single bond between WZ; and when Y=N, W=N, there is a double bond between YW and Z does not exist.

The invention also includes a pharmaceutical composition for inhibiting the enzymatic functions of HIV-reverse transcriptase in a patient wherein the pharmaceutical composition comprises a therapeutically effective amount of the compound of Formula I and a pharmaceutically acceptable carrier. The pharmaceutical composition is also effective in treating AIDS, AIDS related complex, and related disorders.

The invention further includes a method for treating an HIV infection that comprises administering to a patient infected with HIV, a therapeutically effective amount of the compound of Formula I or a pharmaceutically acceptable salt thereof. The method of treating a patient infected with HIV, including an individual that is asymptomatic but tests positive for the HIV antigen, an individual who is symptomatically sick but does not have AIDS related diseases and an individual infected with the HIV virus who has AIDS related diseases. The method further includes treating patients infected by one or more strains of the HIV virus as determined by the presence of either a measurable viral antibody or antigen in the patient's serum, has a symptomatic AID's defining infection including disseminated histoplasmosis, isopsoriasis, bronchial and pulmonary candidiasis, including pneumocystic pneumonia, non Hodgkin's lymphoma and kaposi's sarcoma or has an absolute CD₄ lympocyte count of less than 200/cm³ in the patient's peripheral blood. The administration of the compounds of Formula I is oral and an effective dose is from about 0.01 mg/kg/day to about 500 mg/kg/day. The method includes the compounds of Formula I selected from the group consisting of:

3-[4-(2-Methyl-imidazo[4,5-c]pyridin-1-yl)-benzyl]-3H-benzothiazol-2-one;

6-Fluoro-3-[4-(2-methyl-imidazo[4,5-c]pyridin-1-yl)-benzyl]-3H-benzothiazol-2-one;

3-[4-(2-Ethyl-imidazo[4,5-c]pyridin-1-yl)-benzyl]-3H-benzothiazol-2-one;

3-[4-(2-Isopropyl-imidazo[4,5-c]pyridin-1-yl)-benzyl]-3H-benzothiazol-2-one; and 3-[4-(2-Methyl-imidazo[4,5-c]pyridin-1-yl)-benzyl]-3H-benzooxazol-2-one.

6-Methyl-3-[4-(2-methyl-imidazo[4,5-c]pyridin-1-yl)-benzyl]-3H-benzothiazol-2-one;

6-Ethyl-3-[4-(2-methyl-imidazo[4,5-c]pyridin-1-yl)-benzyl]-3H-benzothiazol-2-one;

6-Isopropyl-3-[4-(2-methyl-imidazo[4,5-c]pyridin-1-yl)-benzyl]-3H-benzothiazol-2-one;

6-Trifluoromethyl-3-[4-(2-methyl-imidazo[4,5-c]pyridin-1-yl)-benzyl]-3H-benzothiazol-2-one;

6-Methoxy-3-[4-(2-methyl-imidazo[4,5-c]pyridin-1-yl)-benzyl]-3H-benzothiazol-2-one;

6-Chloro-3-[4-(2-methyl-imidazo[4,5-c]pyridin-1-yl)-benzyl]-3H-benzothiazol-2-one;

6-Cyano-3-[4-(2-methyl-imidazo[4,5-c]pyridin-1-yl)-benzyl]-3H-benzothiazol-2-one;

5-Methyl-3-[4-(2-methyl-imidazo[4,5-c]pyridin-1-yl)-benzyl]-3H-benzothiazol-2-one;

5-Chloro-3-[4-(2-methyl-imidazo[4,5-c]pyridin-1-yl)-benzyl]-3H-benzothiazol-2-one;

5-Cyano-3-[4-(2-methyl-imidazo[4,5-c]pyridin-1-yl)-benzyl]-3H-benzothiazol-2-one;

5-Methoxy-3-[4-(2-methyl-imidazo[4,5-c]pyridin-1-yl)-benzyl]-3H-benzothiazol-2-one;

5-Fluoro-3-[4-(2-methyl-imidazo[4,5-c]pyridin-1-yl)-benzyl]-3H-benzothiazol-2-one;

5-Trifluoromethyl-3-[4-(2-methyl-imidazo[4, 5-c]pyridin-1-yl)-benzyl]-3H-benzothiazol-2-one;

6-Chloro-3-[4-(2-methyl-imidazo[4,5-c]pyridin-1-yl)-benzyl]-3H-benzooxazol-2-one;

6-Methoxy-3-[4-(2-methyl-imidazo[4,5-c]pyridin-1-yl)-benzyl]-3H-benzooxazol-2-one;

6-Methyl-3-[4-(2-methyl-imidazo[4,5-c]pyridin-1-yl)-benzyl]-3H-benzooxazol-2-one;

5-Chloro-3-[4-(2-methyl-imidazo[4,5-c]pyridin-1-yl)-benzyl]-3H-benzooxazol-2-one;

5-Methyl-3-[4-(2-methyl-imidazo[4,5-c]pyrid in-1-yl)-benzyl]-3H-benzooxazol-2-one;

1-[4-(2-Methyl-imidazo[4,5-c]pyridin-1-yl)-benzyl]-1,3-dihydro-benzoimidazol-2-one;

3-[6-(2-Methyl-imidazo[4, 5-c] pyridin-1-yl)-pyridin-3-ylmethyl]-3H-benzothiazol-2-one;

1-[4-(2-Methyl-imidazo[4,5-c]pyridin-1-yl)-benzyl]-1H-benzotriazole;

2-Methyl-1-[4-(2-methyl-benzoimidazol-1-ylmethyl)-phenyl]-1H-imidazo[4,5-c]pyridine;

3-[2-Methyl-4-(2-methyl-imidazo[4,5-c]pyridin-1-yl)-benzyl]-3H-benzothiazol-2-one;

5,6-Difluoro-3-[4-(2-methyl-imidazo[4,5-c]pyridin-1-yl)-benzyl]-3H-benzothiazol-2-one;

5-Hydroxy-3-[4-(2-methyl-imidazo[4,5-c]pyridin-1-yl)-benzyl]-3H-benzothiazol-2-one Preferably the chosen compounds are:

3-[4-(2-Methyl-imidazo[4,5-c]pyridin-1-yl)-benzyl]-3H-benzothiazol-2-one;

6-Fluoro-3-[4-(2-methyl-imidazo[4,5-c]pyridin-1-yl)-benzyl]-3H-benzothiazol-2-one;

3-[4-(2-Ethyl-imidazo[4,5-c]pyridin-1-yl)-benzyl]-3H-benzothiazol-2-one;

5,6-Difluoro-3-[4-(2-methyl-imidazo[4,5-c]pyridin-1-yl)-benzyl]-3H-benzothiazol-2-one;

3-[4-(2-lsopropyl-imidazo[4,5-c]pyridin-1-yl)-benzyl]-3H-benzothiazol-2-one; and 3-[4-(2-Methyl-imidazo[4,5-c]pyridin-1-yl)-benzyl]-3H-benzooxazol-2-one.

The method of treating the patient infected with HIV virus also includes the administration of the compound of Formula 1 with other inhibitors of biochemical pathways in the virus (eg. protease inhibitors, nucleoside reverse transcriptase inhibitors and non-nucleoside reverse transcriptase inhibitors) such as: AZT, 3TC, Zidovudine, laminvudine, stavudine DMD-266, Ritonavir, Nelfinavir, Abacavir, Indinavir, 141-W94, or Delavirdine or a pharmaceutically acceptable salt or ester thereof.

The term "treating", "treat" or "treatment" as used herein includes preventive (e.g., prophylactic) and palliative treatment.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. The compounds of Formula 1 may also exist as tautomers. This invention relates to the use of all such tautomers and mixtures thereof.

The subject invention also includes isotopically-labelled compounds, and the pharmaceutically acceptable salts thereof, which are identical to those recited in Formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $17^{O,}$ $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of Formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing and methods of treating HIV infections through administering prodrugs of compounds of the Formula 1. Compounds of Formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of Formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

DETAILED DESCRIPTION OF THE INVENTION

The preparation of the compounds of the present invention is described below. Preparation of the compounds of Formula 1 are best carried out by the preparations A and B described below and in the Examples 1–18.

Preparation A entails the formation of an azabenzimidazole ring from an appropriately substituted 3,4-diaminopyridine and a carboxylic acid anhydride. Preparation B involves the hydrolysis of an ester, formed in the previous step, to the requisite alcohol. In the examples, this alcohol is then coupled with various heterocycles to give the claimed compounds of interest.

Preparation A is most commonly performed with lower molecular weight carboxylic acid anhydride as solvent at temperatures between 50 and 200° C., most commonly at 120–160° C. Alternatively, the anhydride can be utilized in combination with a non reactive hydrocarbon, aromatic or ether solvent at the same elevated temperatures.

Preparation B is commonly performed with lower molecular weight alcohols, both with and without water, utilizing an inorganic hydroxide salt, most commonly sodium or potassium hydroxide, at temperatures between 0 and 100° C.

Example 1 is commonly performed with polar aprotic solvents utilizing a strong base, at temperatures between 50 and 150° C.

Example 13 is commonly performed with polar aprotic solvents, most commonly with ether or chlorocarbon solvents, at temperatures between 0 and 100° C. The coupling reagent is most commonly a dialkyl substituted carbodiimide.

Example 16 is commonly performed with polar aprotic solvents, most commonly with ether or chlorocarbon solvents.

Example 17 is commonly performed with polar aprotic solvents, most commonly with ether or chlorocarbon solvents.

The compounds of Formula I possess inhibitory activity against HIV reverse transcriptase. When administered in suitable dosage forms, they are useful in the prevention or treatment of AIDS, ARC (AIDS RELATED COMPLEX) and related disorders associated with HIV infection. Another aspect of the invention, therefore, is a method for treating an HIV infection which comprises administering to a patient, exposed to or infected by HIV a therapeutically effective amount of a novel compound of Formula I, as described above.

The compounds of Formula I may be administered in single or divided doses by the oral, parenteral or topical routes. A suitable oral dosage for a compound of Formula I would be in the range of about 0.2 to 100 mg/kg/dy for patients who are HIV positive but are asymptomatic. ARC (AIDS-related complex) and AIDS patients would be typically treated with higher oral doses (about 1 to about 500-mg/kg/day). The term human retrovirus (HRV) indicates human immunodeficiency virus type I, or strains thereof apparent to one skilled in the art, which belong to the same viral families and which create similar physiological effects in humans as various human retroviruses.

Patients to be treated would include those individuals (1) infected with one or more than one strain of a human retrovirus as determined by the presence of either measurable viral antibody or antigen in the serum and (2) having either a symptomatic AIDS defining infection such as (a) disseminated histoplasmosis, (b) isopsoriasis, (c) bronchial and pulmonary candidiasis including pneumocystis pneumonia (d) non-Hodgkin's lymphoma or (e) Kaposi's sarcoma and being less than sixty years old; or (f) having an absolute CD4 lymphocyte count of less than 200/cm$^3$ in the peripheral blood.

In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration.

Examples of such carrier materials are water, gelatin, talc, starch, magnesium stearate, gum arabic vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of Formula I can be administered in an aqueous or nonaqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered by suppository.

As stated above, the compounds provided by the invention inhibit the enzymatic activity of HIV-1RT. Based upon testing of these compounds, as described below, it is known that they inhibit the RNA-dependent DNA polymerase activity of HIV-1 RT. It is known that they also inhibit the DNA-dependent DNA polymerase activity of HIV-1 RT.

Utilizing the Reverse Transcriptase (RT) Assay described below, compounds can be tested for their ability to inhibit the RNA-dependent DNA polymerase activity of HIV-1 RT. Compounds described in the Examples which appear below, were so tested. The results of this testing appear in Table I, below.

HIV Reverse Transcriptase Assay:

HIV reverse transcriptase activity is assessed by following the incorporation of $^3$H-dCTP into newly synthesized DNA using the natural tRNA$^{Lys3}$ primer annealed to a viral RNA template sequence. Assays are performed in a final volume of 100 µL in 96-well plates. Briefly, assay buffer (50 mM Tris pH 7.5, 50 mM NaCl, 5 mM MgCl$_2$), primer/template (10–60 nM), dNTPs (dATP, dGTP, dTTP; 100 nM each), and $^3$H-dCTP (180 nM) are combined, and the reaction is initiated with 60 nM HIV-RT. After 45 minutes at room temperature, the assay is quenched with 0.1 M EDTA and harvested onto a DEAE filter using a Skatron Harvester with a solution of 5% Na$_2$HPO$_4$-2% sodium pyrophosphate.

The filter mats are dried and placed into a plastic bag with 10 ml of scintillant, and counted on a Wallac BetaPlate reader. Non-specific activity is determined by adding 0.1 M EDTA at the start of the assay.

To assess the activity of compounds on HIV-RT activity, compounds are added to the assay prior to addition of enzyme. Compounds are dissolved in 14% DMSO (0.7% final), and tested at 32, 10, 3.2, 1.0, 0.32, and 0.10 µM in triplicate. % Inhibition is calculated according to the following equation:

$$\% \text{ Inh} = \left[ 1 - \left[ \frac{\text{dpm in presence of compound} - \text{non} - \text{specific dpm}}{\text{dpm in absence of compound} - \text{non} - \text{specific dpm}} \right] \right] \times 100$$

| Compound | % Inhibition at 10 uM |
|---|---|
| 3-[4-(2-Methyl-imidazo[4,5-c]pyridin-1-yl)-benzyl]-3H-benzothiazol-2-one | 78 |
| 6-Fluoro-3-[4-(2-methyl-imidazo[4,5-c]pyridin-1-yl)-benzyl]-3H-benzothiazol-2-one | 76 |
| 3-[4-(2-Ethyl-imidazo[4,5-c]pyridin-1-yl)-benzyl]-3H-benzothiazol-2-one | 72 |
| 3-[4-(2-Isopropyl-imidazo[4,5-c]pyridin-1-yl)-benzyl]-3H-benzothiazol-2-one | 23 |
| 3-[4-(2-Methyl-imidazo[4,5-c]pyridin-1-yl)-benzyl]-3H-benzooxazol-2-one | 61 |
| 6-Methyl-3-[4-(2-methyl-imidazo[4,5-c]pyridin-1-yl)-benzyl]-3H-benzothiazol-2-one | 30 |
| 6-Methoxy-3-[4-(2-methyl-imidazo[4,5-c]pyridin-1-yl)-benzyl]-3H-benzothiazol-2-one | 22 |
| 6-Chloro-3-[4-(2-methyl-imidazo[4,5-c]pyridin-1-yl)-benzyl]-3H-benzothiazol-2-one | 45 |
| 5-Methoxy-3-[4-(2-methyl-imidazo[4,5-c]pyridin-1-yl)-benzyl]-3H-benzothiazol-2-one | 41 |
| 2-Methyl-1-[4-(2-methyl-benzoimidazol-1-ylmethyl)-phenyl]-1H-imidazo[4,5-c]pyridine | 20 |

The present invention is illustrated by the following examples, but is not limited to the details thereof.

The compounds of Formula I and their salts can be prepared by the Preparations A and B. and the Examples 1–18 given below.

Preparation A

Acetic Acid 4-(2-methyl-imidazo[4,5-c]pyridin-1-yl)-benzyl Ester

A solution of 3-amino-4-(4-hydroxymethylphenylamino) pyridine (3.26 g, 15.2 mmol, prepared in U.S. Pat. No. 5,322,847, incorporated by reference) and acetic anhydride (60 mL) was heated at reflux overnight. The reaction was cooled to room temperature and concentrated under vacuum to a viscous oil. The residue was diluted with 2N HCl and washed with methylene chloride (2×50 mL). The remaining aqueous layer was the carefully neutralized with sodium hydrogen carbonate such that the pH was greater than 8, and then extracted with methylene chloride (2×50 mL). The later combined organic layers were dried (MgSO$_4$), filtered and concentrated to give a brown oil. This was purified by chromatography on silica gel utilizing 9:1 CHCl$_3$:EtOH to give 1.25 g of a tan solid. $^1$H NMR (300 MHz, CDCl$_3$) δ 2.10 (s, 3H), 2.55 (s, 3H), 5.16 (s, 2H), 7.36 (d, 2H), 7.42 (d, 1H), 7.59 (d, 2H), 8.44 (d, 1H), 9.02 (s, 1H). $^{13}$C NMR (75 MHz, CDCl$_3$) δ 14.7, 20.9, 65.0, 107.9, 126.9, 130.2,132.9, 134.9, 135.6, 139.2, 139.9, 142.1, 145.2, 159.1. MS Cl (m/e, %) 282 (M+1, 100), 268 (77).

Also prepared by Preparation A were:

Propionic Acid 4-(2-ethyl-imidazo[4,5-c]pyridin-1-yl)-benzyl Ester

Isolated as a brown oil in 96% yield. $^1$H NMR (300 MHz, CDCl$_3$)δ 1.23 (t, 3H), 1.40 (t, 3H), 2.46 (q, 2H), 2.84 (q, 2H), 5.25 (s, 2H), 7.07 (d, 1H), 7.36 (d, 2H), 7.60 (d, 2H), 8.37 (d, 1H), 9.10 (s, 1H).

Isobutyric Acid 4-(2-isopropyl-imidazo[4,5-c]pyridin-1-yl)-benzyl Ester

Isolated as a brown oil in 86% yield. $^1$H NMR (300 MHz, CDCl$_3$)δ 1.25 (d, 6H), 1.36 (d, 6H), 3.10 (m, 2H), 5.24 (s, 2H), 7.03 (d, 1H), 7.36 (d, 2H), 7.60 (d, 2H), 8.38 (d, 1H), 9.11 (s, 1H).

Preparation B

[4-(2-Methyl-imidazo[4,5-c]pyridin-1-yl)-phenyl]-methanol

To a solution of the product of Preparation A (1.25 g, 4.44 mmol) and ethanol (20 mL) was added water (3 mL) and NaOH (355 mg, 8.90 mmol). After stirring for 2 hours at room temperature, an aqueous saturated NaCl solution (10 mL) was added and the mixture was extracted with methylene chloride (2×50 mL). The combined organic layers were dried (MgSO$_4$), filtered and concentrated to give an oil. This was purified by chromatography on silica gel utilizing 9:1 CHCl$_3$:EtOH to give 0.67 g of a white solid. A separate sample was recrystallized from methanol/methylene chloride, mp 265–267° C. $^1$H NMR (300 MHz, CDCl$_3$)δ 2.54 (s, 3H), 4.89 (s, 2H), 7.09 (d, 2H), 7.32 (d, 2H), 7.65 (d, 2H), 8.29 (d, 1H), 8.93 (s, 1H). $^{13}$C NMR (75 MHz, CDCl$_3$)δ 14.3, 63.8, 105.4, 126.6, 128.4, 133.6, 139.6, 141.2, 141.4, 142.0, 143.3, 153.4. MS Cl (m/e, %) 239 (M+1, 100).

Also prepared by Preparation B were:

[4-(2-Ethyl-imidazo[4,5-c]pyridin-1-yl)-phenyl]-methanol

Isolated as a brown solid in 83% yield. $^1$H NMR (300 MHz, CDCl$_3$)δ 1.38 (t, 3H), 2.83 (q, 2H), 4.86 (s, 2H), 7.05 (d, 1H), 7.35 (d, 2H), 7.52 (d, 2H), 8.35 (s, 1H), 9.08 (s, 1H).

[4-(2-Isopropyl-imidazo[4,5-c]pyridin-1-yl)-phenyl]-methanol

Isolated as a brown semi-solid in 95% yield. $^1$H NMR (300 MHz, CDCl$_3$)δ 1.34 (d, 6H), 3.11 (p, 1H), 4.89 (s, 1H), 7.01 (d, 1H), 7.34 (d, 2H), 7.63 (d, 2H), 8.32 (d, 1H), 9.05 (s, 1H).

EXAMPLE 1

3-[4-(2-Methyl-imidazo[4,5-c]pyridin-1-yl)-benzyl]-3H-benzothiazol-2-one

To a solution of the product of Preparation B (211 mg, 0.889 mmol) and dry dimethylformamide was added 95% sodium hydride (22 mg, 0.93 mmol). After stirring for 20 min, 2-chlorobenzothiazole (115 μL, 0.889 mmol) was added in one portion and the reaction heated to 90° C. for 18 hours. After cooling to room temperature, the solution was diluted with water (5 mL) and extracted with ethyl acetate (2×25 mL). The combined organic layers were washed with water (2×5 mL), brine (5 mL), dried (Na$_2$SO$_4$) and concentrated to give an amber oil. This was chromatographed first on silica gel utilizing 10:1 CH$_2$Cl$_2$:MeOH and then on reverse phase (BakerBond™ C18) utilizing 6:4 acetonitrile:water to give the title compound as a white solid, mp 198–201° C. $^1$H NMR (300 MHz, DMSO-d$_6$)δ 2.46 (s, 3H), 5.35 (s, 2H), 7.18 (d, 1H), 7.24 (t, 1H), 7.39 (t, 1H), 7.42 (d, 1H), 7.59 (s, 4H), 7.74 (d, 1H), 8.37 (d, 1H), 8.91 (s, 1H). MS Cl (m/e, %) 373 (M+1, 100), 222 (25), 152 (32).

|  | C | H | N |
|---|---|---|---|
| Anal. Calc'd for C$_{21}$H$_{16}$N$_4$OS: | 67.73 | 4.33 | 15.05 |
| Found | 67.32 | 4.17 | 14.93 |

Also prepared by the method of Example 1 were:

EXAMPLE 2

6-Fluoro-3-[4-(2-methyl-imidazo[4,5-c]pyridin-1-yl)-benzyl]-3H-benzothiazol-2-one Isolated as yellow needles from CH$_2$Cl$_2$/(iPr)$_2$O, mp 223° C.

MS El (m/e, %) 390 (M+, 14), 222 (100).

|  | C | H | N |
|---|---|---|---|
| Anal. Calc'd for C$_{21}$H$_{15}$N$_4$OSF · 0.5H$_2$O: | 63.15 | 4.04 | 14.03 |
| Found | 63.15 | 3.77 | 13.88 |

EXAMPLE 3

3-[4-(2-Ethyl-imidazo[4,5-c]pyridin-1-yl)-benzyl]-3H-benzothiazol-2-one

Isolated as a white solid, mp 194–196° C. $^1$H NMR (300 MHz, CDCl$_3$)δ 1.38 (t, 3H), 2.80 (q, 2H), 5.29 (s, 2H), 7.05 (m, 2H), 7.23 (t, 1H), 7.31 (d, 1H), 7.36 (d, 2H), 7.52 (m, 3H), 8.36 (d, 1H), 9.09 (s, 1H).

MS Cl (m/e, %) 387 (M+1, 100), 238 (22), 152 (30).

|  | C | H | N |
|---|---|---|---|
| Anal. Calc'd for C$_{22}$H$_{18}$N$_4$OS · H$_2$O: | 65.33 | 4.98 | 13.85 |
| Found | 65.50 | 4.73 | 13.63 |

EXAMPLE 4

3-[4-(2-lsopropyl-imidazo[4,5-c]pyridin-1-yl)-benzyl]-3H-benzothiazol-2-one

Isolated as a white solid as a white solid, mp 257–263° C. $^1$H NMR (300 MHz, CDCl$_3$)δ 1.35 (d, 6H), 3.09 (p, 1H), 5.30 (s, 2H), 7.00 (d, 1H), 7.08 (d, 1H), 7.25 (t, 1H), 7.31 (d, 1H), 7.35 (d, 2H), 7.52 (m, 3H), 8.36 (d, 1H), 9.11 (s, 1H). MS Cl (m/e, %) 401 (M+1, 100), 252 (20), 152 (20).

|  | C | H | N |
|---|---|---|---|
| Anal. Calc'd for C$_{23}$H$_{20}$N$_4$OS · 0.5H$_2$O: | 67.46 | 5.17 | 13.68 |
| Found | 67.24 | 5.10 | 13.83 |

EXAMPLE 5

6-Methyl-3-[4-(2-methyl-imidazo[4,5-c]pyridin-1-yl)-benzyl]-3H-benzothiazol-2-one Isolated as a white solid from CH$_2$Cl$_2$/(iPr)$_2$O, mp 195–196° C. $^1$H NMR (300 MHz, DMSO-d$_6$)δ 2.28 (s, 3H), 2.40 (s, 3H), 5.26 (s, 2H), 7.12 (d, J=5.6 Hz, 1H), 7.15 (s, 1H), 7.26 (d, J=8.3 Hz, 1H), 7.49 (s, 1H), 7.51 (d, J=8.3 Hz, 2H), 7.54 (d, J=8.3 Hz, 2H), 8.22 (d, J=5.6 Hz, 1H), 8.85 (s, 1H).

MS CI (m/e, %) 387 (M+1, 100).

|  | C | H | N |
|---|---|---|---|
| Anal. Calc'd for $C_{22}H_{28}N_4OS$: | 68.37 | 4.69 | 14.50 |
| Found | 68.31 | 4.36 | 14.58 |

EXAMPLE 6

6-Methoxy-3-[4-(2-methyl-imidazo[4,5-c]pyridin-1-yl)-benzyl]-3H-benzothiazol-2-one Isolated as a white solid from $CH_2Cl_2/(iPr)_2O$, mp 137–138° C. $^1$H NMR (300 MHz, DMSO-$d_6$) δ 2.40 (s, 3H), 3.71 (s, 3H), 5.25 (s, 2H), 6.92 (dd, J=2.5, 8.7 Hz, 1H), 7.12 (d, J=5.4 Hz, 1H), 7.28 (d, J=9.1 Hz, 1H), 7.37 (d, J=2.5 Hz, 1H), 7.51 (d, J=8.5 Hz, 2H), 7.54 (d, J=8.5 Hz, 2H), 8.22 (d, J=5.4 Hz, 1H), 8.85 (s, 1H).

MS CI (m/e, %) 403 (M+1, 100).

|  | C | H | N |
|---|---|---|---|
| Anal. Calc'd for $C_{22}H_{18}N_4O_2S$: | 65.65 | 4.51 | 13.92 |
| Found | 65.29 | 4.39 | 13.95 |

EXAMPLE 7

6-Chloro-3-[4-(2-methyl-imidazo[4,5-c]pyridin-1-yl)-benzyl]-3H-benzothiazol-2-one Isolated as a white solid from $CH_2Cl_2/(iPr)_2O$, mp 250–251° C. (dec). $^1$H NMR (300 MHz, DMSO-$d_6$) δ 2.42 (s, 3H), 5.31 (s, 2H), 7.14 (d, J=5.8 Hz, 1H), 7.41 (m, 2H), 7.53 (d, J=8.7 Hz, 2H), 7.57 (d, J=8.7 Hz, 2H), 7.90 (m, 1H), 8.24 (d, J=5.4 Hz, 1H), 8.88 (s, 1H).

MS CI (m/e, %) 407,409 (M+1, 100).

|  | C | H | N |
|---|---|---|---|
| Anal. Calc'd for $C_{21}H_{15}ClN_4OS$: | 61.99 | 3.72 | 13.77 |
| Found | 61.60 | 3.50 | 13.76 |

EXAMPLE 8

5-Methoxy-3-[4-(2-methyl-imidazo[4,5-c]pyridin-1-yl)-benzyl]-3H-benzothiazol-2-one Isolated as a white solid from $CH_2Cl_2/(iPr)_2O$, mp 250–251° C. (dec). $^1$H NMR (300 MHz, DMSO-$d_6$) δ 2.41 (s, 3H), 3.73 (s, 3H), 5.28 (s, 2H), 6.81 (dd, J=2.5, 8.7 Hz, 1H), 7.01 (d, J =2 Hz, 1H), 7.14 (d, J=5.4 Hz, 1H), 7.54 (s, 4H), 7.57 (s, 1H), 8.22 (d, J=5.8 Hz, 1H), 8.86 (s, 1H).

MS CI (m/e, %) 403 (M+1, 100).

|  | C | H | N |
|---|---|---|---|
| Anal. Calc'd for $C_{22}H_{18}N_4O_2S \cdot 0.5H_2O$: | 64.22 | 4.65 | 13.62 |
| Found | 64.08 | 4.40 | 13.56 |

EXAMPLE 9

6-Ethyl-3-[4-(2-methyl-imidazo[4,5-c]pyridin-1-yl)-benzyl]-3H-benzothiazol-2-one Isolated as a white solid from $CH_2Cl_2/(iPr)_2O$, mp 147–148° C. (dec). $^1$H NMR (300 MHz, DMSO-$d_6$) δ 1.13 (t, J=7.5 Hz, 3H), 2.40 (s, 3H), 2.58 (q, J=7.5 Hz, 2H), 5.26 (s, 2H), 7.12 (d, J=5.4 Hz, 1H), 7.17(dd, J=1.2, 8.3 Hz, 1H), 7.28 (d, J=8.3 Hz, 1H), 7.53 (m, 5H), 8.22 (d, J=5.4 Hz, 1H), 8.85 (s, 1H).

MS CI (m/e, %)401 (M+1, 100).

|  | C | H | N |
|---|---|---|---|
| Anal. Calc'd for $C_{23}H_{20}N_4OS$: | 68.69 | 5.03 | 13.99 |
| Found | 69.07 | 4.98 | 13.89 |

EXAMPLE 10

5,6-Difluoro-3-[4-(2-methyl-imidazo[4,5-c]pyridin-1-yl)-benzyl]-3H-benzothiazol-2-one Isolated as a white solid from $CH_2Cl_2/(iPr)_2O$, mp 269–270° C. (dec). $^1$H NMR (300 MHz, DMSO-$d_6$) δ 2.42 (s, 3H), 5.28 (s, 2H), 7.14 (d, J=5.8 Hz, 1H), 7.53 (s, 4H), 7.73 (dd, J=6.8, 11.4 Hz, 1H), 7.96 (dd, J=7.9, 10.4 Hz, 1H), 8.24 (d, J=5.4 Hz, 1H), 8.87 (s, 1H).

MS CI (m/e, %) 409 (M+1, 100).

EXAMPLE 11

6-Isopropyl-3-[4-(2-methyl-imidazo[4,5-c]pyridin-1-yl)-benzyl]-3H-benzothiazol-2-one Isolated as a white solid from $CH_2Cl_2/(iPr)_2O$, mp 147–148° C. (dec). $^1$H NMR (300 MHz, CDCl$_3$) δ 1.25 (6, J=6.8 Hz, 6H), 2.51 (s, 3H), 2.93 (sept, J=6.8 Hz, 1H), 5.23 (s, 2H), 6.96 (d, J=8.3 Hz, 1H), 7.05 (dd, J=1.4, 5.8 Hz, 1H), 7.16 (dd, J=1.4, 8.3 Hz, 1H), 7.32 (d, J =8.7 Hz, 2H), 7.35 (d, J=1.4 Hz, 1H), 7.54 (d, J=8.3 Hz, 2H), 8.35 (d, J=5.8 Hz, 1H), 9.03 (s, 1H).

MS CI (m/e, %) 415 (M+1, 100).

|  | C | H | N |
|---|---|---|---|
| Anal. Calc'd for $C_{24}H_{22}N_4OS$: | 69.54 | 5.35 | 13.52 |
| Found | 69.48 | 5.49 | 13.59 |

EXAMPLE 12

5-Hydroxy-3-[4-(2-methyl-imidazo[4,5-c]pyridin-1-yl)-benzyl]-3H-benzothiazol-2-one Isolated as a white solid. $^1$H NMR (300 MHz, MeOH-$d_4$) δ 2.56 (s, 3H), 5.25 (s, 2H), 6.85 (d, J=2.5 Hz, 1H), 6.90 (dd, J=2.5, 8.7 Hz, 1H), 7.30 (m, 1H), 7.36 (d, J=8.7 Hz, 1H), 7.56 (d, J=8.7 Hz, 2H), 7.77 (d, J=8.7 Hz, 2H), 8.30 (s, 1H), 8.91 (s, IH).

MS CI (m/e, %) 389 (M+1, 100).

The following compounds may also be prepared by the method of Example 1 with the appropriately substituted benzothiazole:

6-Trifluoromethyl-3-[4-(2-methyl-imidazo[4,5-c]pyridin-1-yl)-benzyl]-3H-benzothiazol-2-one;
6-Cyano-3-[4-(2-methyl-imidazo[4,5-c]pyridin-1-yl)-benzyl]-3H-benzothiazol-2-one;
5-Methyl-3-[4-(2-methyl-imidazo[4,5-c]pyrid in-1-yl)-benzyl]-3H-benzothiazol-2-one;
5-Chloro-3-[4-(2-methyl-imidazo[4,5-c]pyridin-1-yl)-benzyl]-3H-benzothiazol-2-one;
5-Cyano-3-[4-(2-methyl-imidazo[4,5-c]pyridin-1-yl)-benzyl]-3H-benzothiazol-2-one;
5-Fluoro-3-[4-(2-methyl-imidazo[4,5-c]pyridin-1-yl)-benzyl]-3H-benzothiazol-2-one;
5-Trifluoromethyl-3-[4-(2-methyl-imidazo[4,5-c]pyrid in-1-yl)-benzyl]-3H-benzothiazol-2-one;

EXAMPLE 13

3-[4-(2-Methyl-imidazo[4,5-c]pyridin-1-yl)-benzyl]-3H-benzooxazol-2-one

To a solution of the product of Preparation B (79 mg, 0.33 mmol) and THF (2 mL) was added dicyclohexylcarbodiimide (136 mg, 0.66 mmol). After stirring for 2 days at room temperature, the solvent was removed under vacuum. Benzoxazol-2-one (58 mg, 0.43 mmol) was added and the mixture heated to 150° C. for 90 min and then allowed to cool. The residue was then diluted with methylene chloride (20 mL) and then washed with 10% aqueous KOH (5 mL), water (5 mL), dried ($Na_2SO_4$) and concentrated to give a brown oil. This was chromatographed on silica gel utilizing 9:1 $CH_2Cl_2$:MeOH and then recrystallized from $CH_2Cl_2$/$(iPr)_2O$, to give a yellow solid, mp 84–87° C. $^1$H NMR (300 MHz, DMSO-$d_6$)δ 2.45 (s, 3H), 5.20 (s, 2H), 7.2 (m, 3H), 7.4 (m, 2H), 7.63 (q, 4H), 8.28 (d, 1H), 8.91 (s, 1H).

MS Cl (m/e, %) 357 (M+1, 100), 222 (25), 136 (60).

The following compounds may be prepared by the method of Example 13 with the appropriately substituted benzooxazole:

6-Chloro-3-[4-(2-methyl-imidazo[4,5-c]pyridin-1-yl)-benzyl]-3H-benzooxazol-2-one;
6-Methoxy-3-[4-(2-methyl-imidazo[4,5-c]pyridin-1-yl)-benzyl]-3H-benzooxazol-2-one;
6-Methyl-3-[4-(2-methyl-imidazo[4,5-c]pyridin-1-yl)-benzyl]-3H-benzooxazol-2-one;
5-Chloro-3-[4-(2-methyl-imidazo[4,5-c]pyridin-1-yl)-benzyl]-3H-benzooxazol-2-one;
5-Methyl-3-[4-(2-methyl-imidazo[4,5-c]pyridin-1-yl)-benzyl]-3H-benzooxazol-2-one;

EXAMPLE 14

1-[4-(2-Methyl-imidazo[4, 5-c]pyridin-1-yl)-benzyl]-1,3-dihydro-benzoimidazol-2-one This may be prepared from the product of preparation B, 1–10 equivalents of the appropriately substituted benzoimidazol-2-one, 1–10 equivalents of triphenylphosphine and about 1–10 equivalents of diethylazodicarboxylate, under Mitsunobu conditions, at temperatures between about −20 and 100° C.

EXAMPLE 15

3-[6-(2-Methyl-imidazo[4,5-c]pyridin-1-yl)-pyridin-3-ylmethyl]-3H-benzothiazo1-2-one This may be prepared in a manner similar to Example 1, however substituting an appropriately substituted 2-amino pyridine instead of 4-aminobenzyl alcohol.

EXAMPLE 16

2-Methyl-1-[4-(2-methyl-benzoimidazol-1-ylmethyl)-phenyl]1H-imidazo[4,5-c]pyridine To a solution of the product of Preparation B (400 mg, 1.67 mmol), triphenylphosphine (657 mg, 2.51 mmol), 2-methylbenzimidazole (221 mg, 1.67 mmol) and THF (16 mL) was added diethylazodicarboxylate (437 mg, 2.51 mmol) in a dropwise fashion. After heating at 55° C. for 20 h, the reaction mixture was concentrated and purified by chromatography on silica gel utilizing EtOH/$CH_2Cl_2$ as eluent. The resulting solid was recrystallized from $CH_2Cl_2$/$(iPr)_2O$ to give the title compound isolated as a white solid, mp 184–185° C. $^1$H NMR (300 MHz, DMSO-$d_6$)δ 2.42 (s, 3H), 2.55 (s, 3H), 5.60 (s, 2H), 7.15 (m, 3H), 7.35 (d, J=8.3 Hz, 2H), 7.55 (m, 4H), 8.24 (d, J=5.4 Hz, 1H), 8.88 (s, 1H).

MS Cl (m/e, %) 354 (M+1, 100).

|  | C | H | N |
|---|---|---|---|
| Anal. Calc'd for $C_{22}H_{19}N_5 \cdot 0.25H_2O$: | 73.82 | 5.49 | 19.57 |
| Found | 73.85 | 5.41 | 19.84 |

EXAMPLE 17

1-[4-(2-Methyl-imidazo[4,5-c]pyridin-1-yl)-benzyl]-1H-benzotriazole

The reaction is similar to Example 16, with the exception of substituting 1H-benzotriazole (instead of 2-methylbenzimidazole). The product was purified first on silica gel utilizing EtOH/$CH_2Cl_2$ as eluent, followed by preparative TLC on reverse phase utilizing $H_2O$/MeOH as eluent. The resulting solid was recrystallized from $CH_2Cl_2$/$(iPr)_2O$ to give the title compound isolated as a white solid, mp 126–127° C. $^1$H NMR (300 MHz, MeOH-$d_4$)δ 2.50 (s, 3H), 6.11 (s, 2H), 7.22 (d, J=0.8, 5.8 Hz, 1H), 7.46 (t, J=7.5 Hz, 1H), 7.52 (d, J=8.5 Hz, 2H), 7.58 (t, J=7.5 Hz, 1H), 7.63 (d, J=8.5 Hz, 2H), 7.80 (t, J=8.7 Hz, 1H), 8.03 (d, J=8.3 Hz, 1H), 8.27 (d, J=5.4 Hz, 1H), 8.85 (s, 1H).

MS Cl (m/e, %) 341 (M+1, 100).

|  | C | H | N |
|---|---|---|---|
| Anal. Calc'd for $C_{20}H_{16}N_6 \cdot 0.25H_2O$: | 69.65 | 4.82 | 24.37 |
| Found | 69.76 | 4.68 | 24.25 |

EXAMPLE 18

3-[2-Methyl-4-(2-methyl-imidazo[4,5-c]pyridin1-yl)-benzyl]-3H-benzothiazol-2-one This may be prepared in a manner similar to Example 1, however utilizing 3-amino-4-(4-hydroxymethyl-3methylphenylamino)pyridine instead of 3amino-4(4-hydroxymethylphenylamino)pyridine.

We claim:
1. The method of inhibiting the enzymatic functions of HIV-reverse transcriptase in a patient which comprises administering to a patient infected with HIV-reverse transcriptase a therapeutically effective amount of the compound of Formula I or a pharmaceutically acceptable salt thereof and a pharmaceutically acceptable carrier.

(I)

[Chemical structure of Formula I showing a bicyclic system with substituents $R_1$, $R_2$, $R_3$, $R_5$, W, Y, Z, X, and $(R^3)_n$]

n is an integer from 1 to 4

X is CHI or N;

$R^1$ is H, $(C_1-C_6)$alkyl or $(C_1-C_6)$ alkoxy;

$R^2$ is H, $(C_1-C_6)$alkyl or $(C_1-C_6)$ alkoxy;

each $R^3$ is independently selected from H, $(C_1-C_6)$alkyl $(C_1-C_6)$ alkyloxy, $(C_1-C_6)$ alkylthio, halo, nitro, cyano, ethynyl, hydroxy and trifluoromethyl; and $R^4$ is H, $(C_1-C_6)$alkyl or $(C_1-C_6)$ alkoxy;

$R^5$ is H, $(C_1-C_6)$alkyl or $(C_1-C_6)$ alkyloxy, trifluoromethyl; and

W is N or C;

Y is $N(R^4)$, N, S or O

Z is $R^4$, $NR^4H$, O, or OH;
provided that when Y=$NR^4$, W=C, Z=O, there is a single bond between YW and a double bond between WZ;

when Y=O or S, W=C, Z=O, there is a single bond between YW and a double bond between WZ;

when Y=N, W=C, Z=$R^4$ or $NHR^4$, there is a double bond between YW and a single bond between WZ; and when Y=N, W=N, there is a double bond between YW and Z does not exist.

2. A method of treating AIDS, AIDS related complex and related disorders in a patient which comprises administering to said patient infected with AIDS, AIDS related complex and related disorders a therapeutically effective amount of a compound of formula 1 or a pharmaceutically acceptable salt thereof and a pharmaceutically acceptable carrier.

3. A method for treating an HIV infection which comprises administering to a patient infected with an HIV virus a therapeutically effective amount of the compound according to claim 1 or a pharmaceutically acceptable salt thereof and a pharmaceutically acceptable carrier.

4. A method of treating a patient infected with HIV according to claim 3 wherein (1) an infected individual is asymptomatic but tests positive for the HIV antigen, (2) an infected individual is symptomatically sick but does not have AIDS related disease or (3) an individual infected with the HIV virus has AIDS related diseases.

5. The method of claim 4 wherein patient is (1) infected with one Jr more strains of the a HIV virus as determined by the presence of either measurable viral antibody or antigen in the patient's serum, (2) has asymptomatic AIDS defining infection including disseminated histoplasmosis, isopsoriasis, bronchial and pulmonary candidiasis including pneumocystic pneumonia, non Hodgkin's lymphoma and Kaposi's Sarcoma or has an absolute CD4 lymphocyte count of less than 200/cm$^3$ in the patient's peripheral blood.

6. A method for treating a patient infected with an HIV virus according to claim 3 wherein the administration is oral and an effective dose is from about 0.20 mg/kg/day to about 500 mg/kg/day.

7. A method for treating a mammal infected with the HIV virus wherein the compounds according to claim 1 were selected from the group consisting of 3-[4-(2-Methyl-imidazo[4,5-c]pyridin-1-yl)-benzyl]-3H-benzothiazol-2-one;

6-Fluoro-3-[4-(2-methyl-imidazo[4,5-c]pyridin-1-yl)-benzyl]-3H-benzothiazol-2-one;

3-[4-(2-Ethyl-imidazo[4,5-c]pyridin-1-yl)-benzyl]-3H-benzothiazol-2-one;

3-[4-(2-lsopropyl-imidazo[4,5-c]pyridin-1-yl)-benzyl]-3H-benzothiazol-2-one; and 3-[4-(2-Methyl-imidazo[4,5-c]pyridin-1-yl)-benzyl]-3H-benzooxazol-2-one.

6-Methyl-3-[4-(2-methyl-imidazo[4,5-c]pyridin-1-yl)-benzyl]-3H-benzothiazol-2-one;

6-Ethyl-3-[4-(2-methyl-imidazo[4,5-c]pyridin-1-yl)-benzyl]-3H-benzothiazol-2-one;

6-Isopropyl-3-[4-(2-methyl-imidazo[4,5-c]pyridin-1-yl)-benzyl]-3H-benzothiazol-2-one;

6-Trifluoromethyl-3-[4-(2-methyl-imidazo[4,5-c]pyridin-1-yl)-benzyl]-3H-benzothiazol-2-one;

6-Methoxy-3-[4-(2-methyl-imidazo[4,5-c]pyridin-1-yl)-benzyl]-3H-benzothiazol-2-one;

6-Chloro-3-[4-(2-methyl-imidazo[4,5-c]pyridin-1-yl)-benzyl]-3H-benzothiazol-2-one;

6-Cyano-3-[4-(2-methyl-imidazo[4,5-c]pyridin-1-yl)-benzyl]-3H-benzothiazol-2-one;

5-Methyl-3-[4-(2-methyl-imidazo[4,5-c]pyridin-1-yl)-benzyl]-3H-benzothiazol-2-one;

5-Chloro-3-[4-(2-methyl-imidazo[4,5-c]pyridin-1-yl)-benzyl]-3H-benzothiazol-2-one;

5-Cyano-3-[4-(2-methyl-imidazo[4,5-c]pyridin-1-yl)-benzyl]-3H-benzothiazol-2-one;

5-Methoxy-3-[4-(2-methyl-imidazo[4,5-c]pyridin-1-yl)-benzyl]-3H-benzothiazol-2-one;

5-Fluoro-3-[4-(2-methyl-imidazo[4,5-c]pyridin-1-yl)-benzyl]-3H-benzothiazol-2-one;

5-Trifluoromethyl-3-[4-(2-methyl-imidazo[4,5-c]pyridin-1-yl)-benzyl]-3H-benzothiazol-2-one;

6-Chloro-3-[4-(2-methyl-imidazo[4,5-c]pyridin-1-yl)-benzyl]-3H-benzooxazol-2-one;

6-Methoxy-3-[4-(2-methyl-imidazo[4,5-c]pyridin-1-yl)-benzyl]-3H-benzooxazol-2-one;

6-Methyl-3-[4-(2-methyl-imidazo[4,5-c]pyridin-1-yl)-benzyl]-3H-benzooxazol-2-one;

5-Chloro-3-[4-(2-methyl-imidazo[4,5-c]pyridin-1-yl)-benzyl]-3H-benzooxazol-2-one;

5-Methyl-3-[4-(2-methyl-imidazo[4,5-c]pyridin-1-yl)-benzyl]-3H-benzooxazol-2-one;

1-[4-(2-Methyl-imidazo[4,5-c]pyridin-1-yl)-benzyl]-1,3-dihydro-benzoimidazol-2-one;

3-[6-(2-Methyl-imidazo[4,5-c]pyridin-1-yl)-pyridin-3-ylmethyl]-3H-benzothiazol-2-one;

1-[4-(2-Methyl-imidazo[4, 5-c]pyridin-1-yl)-benzyl]-1 H-benzotriazole;

2-Methyl-1-[4-(2-methyl-benzoimidazol-1-ylmethyl)-phenyl]-1H-imidazo[4,5-c]pyridine;

5,6-Difluoro-3-[4-(2-methyl-imidazo[4,5-c]pyridin-1-yl)-benzyl]-3H-benzothiazol-2-one;

5-Hydroxy-3-[4-(2-methyl-imidazo[4,5-c]pyridin-1-yl)-benzyl]-3H-benzothiazol-2-one;

3-[2-Methyl-4-(2-methyl-imidazo[4,5-c]pyridin-1-yl)-benzyl]-3H-benzothiazol-2-one.

8. A method for treating a mammal infected with HIV virus according to claim 7 wherein the compounds of Formula 1 were selected from the group consisting of:

3-[4-(2-Methyl-imidazo[4,5-c]pyridin-1-yl)-benzyl]-3H-benzothiazol-2-one;

6-Fluoro-3-[4-(2-methyl-imidazo[4,5-c]pyridin-1-yl)-benzyl]-3H-benzothiazol-2-one;

3-[4-(2-Ethyl-imidazo[4,5-c]pyridin-1-yl)-benzyl]-3H-benzothiazol-2-one;

5,6-Difluoro-3-[4-(2-methyl-imidazo[4,5-c]pyridin-1-yl)-benzyl]-3H-benzothiazol-2-one;

3-[4-(2-Isopropyl-imidazo[4,5-c]pyridin-1-yl)-benzyl]-3H-benzothiazol-2-one; and 3-[4-(2-Methyl-imidazo[4,5-c]pyridin-1-yl)-benzyl]-3H-benzooxazol-2-one.

9. A method of treating a patient infected with HIV virus according to claim 3 wherein the administration of the compound of formula I is in combination with AZT, 3TC Zidovudine, Lamivudine, Stavudine DMP-266, Ritonavir, Nelfinavir, Abacavir, Indinavir, 141-W94, or Delavirdine or a pharmaceutically acceptable salt or ester thereof.

* * * * *